US009550725B2

(12) United States Patent
Strautmann et al.

(10) Patent No.: US 9,550,725 B2
(45) Date of Patent: Jan. 24, 2017

(54) LIPOPHILIC POLYALKYLENEPOLYAMINES BY HOMOGENEOUSLY CATALYZED ALCOHOL AMINATION

(71) Applicant: BASF SE, Ludwigshafen (DE)

(72) Inventors: Julia Strautmann, Mannheim (DE); Thomas Schaub, Neustadt (DE); Stephan Hueffer, Ludwigshafen (DE); Steffen Maas, Bubenheim (DE); Claudia Wood, Weinheim (DE)

(73) Assignee: BASF SE, Ludwigshafen (DE)

( * ) Notice: Subject to any disclaimer, the term of this patent is extended or adjusted under 35 U.S.C. 154(b) by 65 days.

(21) Appl. No.: 14/359,134

(22) PCT Filed: Nov. 19, 2012

(86) PCT No.: PCT/EP2012/072944
§ 371 (c)(1),
(2) Date: May 19, 2014

(87) PCT Pub. No.: WO2013/076025
PCT Pub. Date: May 30, 2013

(65) Prior Publication Data
US 2014/0305339 A1    Oct. 16, 2014

(30) Foreign Application Priority Data

Nov. 25, 2011  (EP) ..................................... 11190791

(51) Int. Cl.
*C07C 209/14*  (2006.01)
*C08G 73/02*   (2006.01)
*C09J 179/02*  (2006.01)

(52) U.S. Cl.
CPC ......... *C07C 209/14* (2013.01); *C08G 73/0213* (2013.01); *C09J 179/02* (2013.01)

(58) Field of Classification Search
CPC .... C07C 209/14; C08G 73/0213; C09J 179/02
See application file for complete search history.

(56) References Cited

U.S. PATENT DOCUMENTS

| | | | |
|---|---|---|---|
| 3,708,539 A | 1/1973 | Fenton | |
| 4,324,724 A * | 4/1982 | Mueller | C10M 169/00 528/422 |
| 5,030,740 A | 7/1991 | Bowman et al. | |
| 5,556,619 A | 9/1996 | Royce et al. | |
| 5,726,284 A | 3/1998 | Figuly et al. | |
| 8,637,709 B2 | 1/2014 | Schaub et al. | |
| 8,697,834 B2 | 4/2014 | Schaub et al. | |
| 8,785,693 B2 | 7/2014 | Schaub et al. | |
| 2012/0232293 A1 | 9/2012 | Schaub et al. | |
| 2012/0232294 A1 | 9/2012 | Schaub et al. | |
| 2013/0137901 A1 | 5/2013 | Strautmann et al. | |

FOREIGN PATENT DOCUMENTS

| | | | |
|---|---|---|---|
| CA | 2039316 | * | 10/1991 |
| EP | 0 034 480 A2 | | 8/1981 |
| EP | 0093983 | * | 11/1983 |
| EP | 0 239 934 A2 | | 10/1987 |
| JP | 54-80400 A | | 6/1979 |
| WO | WO 97/23546 A1 | | 7/1997 |
| WO | WO 2011/151268 A1 | | 12/2011 |

OTHER PUBLICATIONS

Abbott et al., "Detailed Investigation of the Radical-Induced Destruction of Chemical Warfare Agent Simulants in Aqueous Solution," J. Phys. Chem., B, 2010, 114, 7681-7685.*
International Search Report issued Mar. 19, 2013, in PCT/EP2012/072944 filed Nov. 19, 2012 with English translation.
Ulrich Steuerle, et al., "Aziridines", Ullman's Encyclopedia of Industrial Chemistry, vol. 4, 2012, pp. 515-522.
Yoshihisa Watanabe, et al., "The Ruthenium Catalyzed N-Alkylation and N-Heterocyclization of Aniline Using Alcohols and Aldehydes", Tetrahedron Letters, vol. 22, No. 28, 1981, pp. 2667-2670.
Ken-ichi Fujita, et al., "Cp*Ir Complex-Catalyzed Hydrogen Transfer Reactions Directed toward Environmentally Benign Organic Synthesis", Synlett, No. 4, Feb. 22, 2005, pp. 560-571.
Annegret Tillack, et al., "Salt-Free Synthesis of Tertiary Amines by Ruthenium-Catalyzed Amination of Alcohols", Eur. J. Org. Chem., 2008, pp. 4745-4750.

(Continued)

*Primary Examiner* — Paul A Zucker
*Assistant Examiner* — Mark Luderer
(74) *Attorney, Agent, or Firm* — Oblon, McClelland, Maier & Neustadt, L.L.P.

(57) ABSTRACT

Process for the preparation of lipophilic polyalkylenepolyamines by homogeneously catalyzed alcohol amination, where aliphatic amino alcohols are reacted with one another or aliphatic diamines or polyamines are reacted with aliphatic diols or polyols with the elimination of water in the presence of a homogeneous catalyst, at least one of the reactants comprising an alkyl or alkylene group having five or more carbon atoms, and after the reaction a phase separation into at least one apolar phase and at least one polar phase being present, the lipophilic polyalkylenepolyamines being present in enriched form in the apolar phase. Polyalkylenepolyamines obtainable by such processes, and polyalkylenepolyamines comprising hydroxyl groups, secondary amines or tertiary amines. Uses of such polyalkylenepolyamines as adhesion promoters for printing inks, adhesion promoters in composite films, cohesion promoters for adhesives, crosslinkers/curing agents for resins, primers in paints, wet-adhesion promoters for emulsion paints, complexing agents and flocculating agents, penetration assistants in wood preservation, corrosion inhibitors, immobilizing agents for proteins and enzymes.

17 Claims, No Drawings

(56) References Cited

OTHER PUBLICATIONS

Annegret Tillack, et al., "A novel ruthenium-catalyzed amination of primary and secondary alcohols", Tetrahedron Letters, 47, 2006, pp. 8881-8885.

M. Haniti, et al., "Ruthenium-Catalyzed N-Alkylation of Amines and Sulfonamides Using Borrowing Hydrogen Methodology", J. Am. Chem. Soc., Jan. 21, 2009, 131, pp. 1766-1774.

Chidambaram Gunanathan, et al., "Selective Synthesis of Primary Amines Directly from Alcohols and Ammonia", Angew. Chem. Int. Ed., 47, 2008, pp. 8661-8664.

U.S. Appl. No. 14/357,822, filed May 13, 2014, Strautmann, et al.
U.S. Appl. No. 14/356,281, filed May 5, 2014, Ebert, et al.

* cited by examiner

LIPOPHILIC POLYALKYLENEPOLYAMINES BY HOMOGENEOUSLY CATALYZED ALCOHOL AMINATION

CROSS-REFERENCE TO RELATED APPLICATIONS

This application is a National Stage of PCT/EP2012/072944 filed on Nov. 19, 2012. This application is based upon and claims the benefit of priority to European Application No. 11190791.1 filed on Nov. 25, 2011.

The present invention relates to processes for the preparation of lipophilic polyalkylenepolyamines by homogeneous-catalyzed alcohol amination of aliphatic amino alcohols (alkanolamines) or of di- or polyamines with diols or polyols. Furthermore, the invention also relates to polyalkylenepolyamines obtainable by these processes and to the use of such polyalkylenepolyamines. The invention further provides specific polyalkylenepolyamines having hydroxyl groups, secondary amine groups or tertiary amine groups.

Further embodiments of the present invention can be found in the claims, the description and the examples. It goes without saying that the features of the subject matter according to the invention that have been specified above and are still to be explained below can be used not only in the combination specifically stated in each case, but also in other combinations, without departing from the scope of the invention. The embodiments of the present invention in which all features have the preferred or very preferred meanings are preferred or very preferred, respectively.

Polyethyleneimines are valuable products with a large number of different uses. For example, polyethyleneimines are used: a) as adhesion promoters for printing inks for laminate films; b) as auxiliaries (adhesion) for producing multi-ply composite films, where not only are different polymer layers compatibilized, but also metal films; c) as adhesion promoters for adhesives, for example in conjunction with polyvinyl alcohol, butyrate and acetate and styrene copolymers, or as cohesion promoter for label adhesives; d) low molecular weight polyethyleneimines can moreover be used as crosslinkers/hardeners in epoxy resins and polyurethane adhesives; e) as primers in coating applications for improving adhesion on substrates such as glass, wood, plastic and metal; f) for improving wet adhesion in standard emulsion paints and also for improving the instantaneous rain resistance of paints for example for road markings; g) as complexing agent with high binding capacity for heavy metals such as Hg, Pb, Cu, Ni and flocculants in water treatment/water processing; h) as penetration auxiliaries for active metal salt formulations in wood preservation; i) as corrosion inhibitors for iron and nonferrous metals; j) for the immobilization of proteins and enzymes. For these applications, it is also possible to use hydrophilic, ambiphilic and lipophilic polyalkylenepolyamines which are not derived from the ethyleneimine.

Polyethyleneimines are currently obtained by the homopolymerization of ethyleneimine. Ethyleneimine is a highly reactive, corrosive and toxic intermediate (aziridines, Ulrich Steuerle, Robert Feuerhake; in Ullmann's Encyclopedia of Industrial Chemistry, 2006, Wiley-VCH, Weinheim).

For the preparation of polyalkylenepolyamines —[$(CH_2)_xN$]— with alkylene groups>$C_2$ (X>2) not derived from aziridine, there are no processes analogous to the aziridine route, as a result of which there has hitherto been no cost-effective process for their preparation.

The homogenously catalyzed amination of alcohols is known from the literature for the synthesis of primary, secondary and tertiary amines starting from alcohols and amines, with monomeric products being obtained in all of the described embodiments.

U.S. Pat. No. 3,708,539 describes the synthesis of primary, secondary and tertiary amines using a ruthenium-phosphane complex.

Y. Watanabe, Y. Tsuji, Y. Ohsugi Tetrahedron Lett. 1981, 22, 2667-2670 reports on the preparation of arylamines by the amination of alcohols with aniline using [$Ru(PPh_3)_3Cl_2$] as catalyst.

EP 0 034 480 A2 discloses the preparation of N-alkyl- or N,N-dialkylamines by the reaction of primary or secondary amines with a primary or secondary alcohol using an iridium, rhodium, ruthenium, osmium, platinum, palladium or rhenium catalyst.

EP 0 239 934 A1 describes the synthesis of mono- and diaminated products starting from diols such as ethylene glycol and 1,3-propanediol with secondary amines using ruthenium and iridium phosphane complexes.

K. I. Fujita, R. Yamaguchi Synlett, 2005, 4, 560-571 describes the synthesis of secondary amines by the reaction of alcohols with primary amines and also the synthesis of cyclic amines by the reaction of primary amines with diols by ring closure using iridium catalysts.

In A. Tillack, D. Hollmann, K. Mevius, D. Michalik, S. Elgin, M. Beller Eur. J. Org. Chem. 2008, 4745-4750, in A. Tillack, D. Hollmann, D. Michalik, M. Beller Tetrahedron Lett. 2006, 47, 8881-8885, in D. Hollmann, S. Bahn, A. Tillack, M. Beller Angew. Chem. Int. Ed. 2007, 46, 8291-8294 and in M. Haniti, S. A. Hamid, C. L. Allen, G. W. Lamb, A. C. Maxwell, H. C. Maytum, A. J. A. Watson, J. M. J. Williams J. Am. Chem. Soc, 2009, 131, 1766-1774 syntheses of secondary and tertiary amines starting from alcohols and primary or secondary amines using homogeneous ruthenium catalysts are described.

The synthesis of primary amines by reacting alcohols with ammonia using a homogeneous ruthenium catalyst is reported in C. Gunanathan, D. Milstein Angew. Chem. Int. Ed. 2008, 47, 8661-8664.

Our unpublished application PCT/EP2011/058758 describes general processes for the preparation of polyalkylenepolyamines by catalytic alcohol amination of alkanolamines or of diamines or polyamines with diols or polyols.

It is an object of the present invention to find a process for the preparation of lipophilic polyalkylenepolyamines in which no undesired coproducts, for example ammonia, are formed.

These and other objects are achieved, as is evident from the disclosure content of the present invention, by the various embodiments of the process of the invention for the preparation of lipophilic polyalkylenepolyamines by homogeneously catalyzed alcohol amination, in which (i) aliphatic amino alcohols are reacted with one another or
(ii) aliphatic diamines or polyamines are reacted with aliphatic diols or polyols with the elimination of water in the presence of a homogeneous catalyst, where at least one of the reactants—aliphatic amino alcohols, aliphatic diamines or polyamines or aliphatic diols or polyols—comprises an alkyl or alkylene group having five or more, preferably seven or more, more preferably nine or more carbon atoms, and after the reaction, preferably after cooling, more particularly to room temperature, preferably after addition of a solvent, preferably a polar solvent, more particularly water, a phase separation into at least one apolar phase and at least one polar phase is present, where the lipophilic polyalkylenepolyamines are present in enriched form in the apolar phase.

Lipophilic polyalkylenepolyamines are fat-soluble polyamines which are synthesized from monomers containing alkyl or alkylene groups having five or more carbon atoms.

By room temperature is meant 21° C. After the reaction, the reaction mixture is preferably cooled. Advantageously, the cooling takes place to ambient temperature, more particularly to room temperature. Cooling generally assists the phase separation into an apolar phase and a polar phase.

A homogeneous catalyst is a catalyst which during the reaction is present in homogeneous solution in the reaction medium.

Within the context of this invention, expressions of the form $C_a$-$C_b$ refer to chemical compounds or substituents with a certain number of carbon atoms. The number of carbon atoms can be selected from the entire range from a to b, including a and b, a is at least 1 and b is always greater than a. The chemical compounds or substituents are further specified by expressions of the form $C_a$-$C_b$-V. V here stands for a chemical compound class or substituent class, for example alkyl compounds or alkyl substituents.

Specifically, the collective terms stated for the various substituents have the following meaning:

$C_1$-$C_{50}$-Alkyl: straight-chain or branched hydrocarbon radicals having up to 50 carbon atoms, for example $C_1$-$C_{10}$-alkyl or $C_{11}$-$C_{20}$-alkyl, preferably $C_1$-$C_{10}$-alkyl, for example $C_1$-$C_3$-alkyl, such as methyl, ethyl, propyl, isopropyl, or C4-C6-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_{10}$-alkyl, such as heptyl, octyl, 2-ethylhexyl, 2,4,4-trimethylpentyl, 1,1,3,3-tetramethylbutyl, nonyl or decyl, and isomers thereof.

$C_3$-$C_{15}$-Cycloalkyl: monocyclic, saturated hydrocarbon groups having from 3 up to 15 carbon ring members, preferably $C_3$-$C_8$-cycloalkyl such as cyclopropyl, cyclobutyl, cyclopentyl, cyclohexyl, cycloheptyl or cyclooctyl, and also a saturated or unsaturated cyclic system such as e.g. norbornyl or norbenzyl.

Aryl: a mono- to trinuclear aromatic ring system comprising 6 to 14 carbon ring members, e.g. phenyl, naphthyl or anthracenyl, preferably a mono- to dinuclear, particularly preferably a mononuclear, aromatic ring system.

Within the context of the present invention, the symbol "*" indicates, for all chemical compounds, the valence via which one chemical group is bonded to another chemical group.

The present invention is elucidated in detail below.

In accordance with the invention, lipophilic polyalkylenepolyamines, as already described, are obtained by reaction of (i) aliphatic amino alcohols with one another, with elimination of water, or of (ii) aliphatic diamines or polyamines with aliphatic diols or polyols, with elimination of water, in each case in the presence of a catalyst.

Suitable aliphatic amino alcohols comprise at least one primary or secondary amino group and at least one OH group and at least one lipophilic alkylene or alkyl group having five or more carbon atoms. Examples are linear, branched or cyclic alkanolamines such as aminodimethylpentanol, for example 5-amino-2,2-dimethylpentanol or 3-amino-2,4-dimethyl-2-pentanol, aminohexanol, for example 2-aminohexan-1-ol, aminoheptanol, for example 2-aminoheptan-1-ol, aminooctanol, for example 2-aminooctan-1-ol, aminononanol, for example 2-aminononan-1-ol, aminodecanol, for example 2-aminodecan-1-ol, aminoundecanol, for example 2-aminoundecan-1-ol, aminododecanol, for example 2-aminododecan-1-ol, aminotridecanol, for example 2-aminotridecan-1-ol.

Suitable aliphatic diamines comprise at least two primary or at least one primary and one secondary or at least two secondary amino groups, they preferably comprise two primary amino groups. Examples are linear, branched or cyclic aliphatic diamines. Examples are ethylenediamine, 1,3-propylenediamine, 1,2-propylenediamine, butylenediamine, for example 1,4-butylenediamine or 1,2-butylenediamine, diaminopentane, for example 1,5-diaminopentane or 1,2-diaminopentane, 1,5-diamino-2-methylpentane, diaminohexane, for example 1,6-diaminohexane or 1,2-diaminohexane, diaminoheptane, for example 1,7-diaminoheptane or 1,2-diaminoheptane, diaminooctane, for example 1,8-diaminooctane or 1,2-diaminooctane, diaminononane, for example 1,9-diaminononane or 1,2-diaminononane, diaminodecane, for example 1,10-diaminodecane or 1,2-diaminodecane, diaminoundecane, for example 1,11-diaminoundecane or 1,2-diaminoundecane, diaminododecane, for example 1,12-diaminododecane or 1,2-diaminododecane, 3,3"-dimethyl-4,4"-diaminodicyclohexylmethane, 4,4'-diaminodicyclohexylmethane, isophoronediamine, 2,2-dimethylpropane-1,3-diamine, 4,7,10-trioxamidecane-1,13-diamine, 4,9-dioxadodecane-1,12-diamine, polyetheramines, piperazine, 3-(cyclohexylamino)propylamine, 3-(methylamino)propylamine, N,N-bis(3-amino-propyl)methylamine.

Suitable aliphatic diols are linear, branched or cyclic aliphatic diols. Examples of aliphatic diols are ethylene glycol, 1,2-propylene glycol, 1,3-propylene glycol, 2-methyl-1,3-propanediol, butanediols, for example 1,4-butylene glycol or butane-2,3-diol or 1,2-butylene gylcol, pentanediols, for example neopentyl glycol or 1,5-pentanediol or 1,2-pentanediol, hexanediols, for example 1,6-hexanediol or 1,2-hexanediol, heptanediols, for example 1,7-heptanediol or 1,2-heptanediol, octanediols, for example 1,8-octanediol or 1,2-octanediol, nonanediols, for example 1,9-nonanediol or 1,2-nonanediol, decanediols, for example 1,10-decanediol or 1,2-decanediol, undecanediols, for example 1,11-undecanediol or 1,2-undecanediol, dodecanediols, for example 1,12-dodecanediol, 1,2-dodecanediol, tridecanediols, for example 1,13-tridecanediol or 1,2-tridecanediol, tetradecanediols, for example 1,14-tetradecanediol or 1,2-tetradecanediol, pentadecanediols, for example 1,15-pentadecanediol or 1,2-pentadecanediol, hexadecanediols, for example 1,16-hexadecanediol or 1,2-hexadecanediol, heptadecanediols, for example 1,17-heptadecanediol or 1,2-heptadecanediol, octadecanediols, for example 1,18-octadecanediol or 1,2-octadecanediol, 3,4-dimethyl-2,5-hexanediol, polyTHF, 1,4-bis(2-hydroxyethyl)piperazine, diethanolamines, for example butyldiethanolamine or methyldiethanolamine.

In accordance with the invention the lipophilic polyalkylenepolyamines are also prepared from aliphatic diols having five or more carbon atoms and aliphatic diamines, or from aliphatic diols and aliphatic diamines having five or more carbon atoms, or from aliphatic diols having five or more carbon atoms and aliphatic diamines having five or more carbon atoms.

In one preferred embodiment of the process according to the invention at least one of the starting materials aliphatic amino alcohols, aliphatic diamines or polyamines or aliphatic diols or polyols comprises an alkyl or alkylene group having from 5 to 50, preferably from 5 to 20, particularly preferably from 6 to 18, very particularly preferably from 7 to 16, especially preferably from 8 to 14 and in particular from 9 to 12 carbon atoms.

Further preferred polyalkylenepolyamines obtainable according to the invention comprise $C_5$-$C_{50}$-alkylene units or alkyl units, particularly preferably $C_8$-$C_{20}$-alkylene units or alkyl units. These can be linear or branched, they are preferably linear. Examples are 1,2-octylene, 1,2-nonylene, 1,2-decylene, 1,2-undecylene, 1,2-dodecylene, 1,2-tridecylene, 1,8-octylene, 1,9-nonylene, 1,10-decylene, 1,11-undecylene, 1,12-dodecylene, 1,13-tridecylene, octyl, nonyl, decyl, undecyl, dodecyl, tridecyl.

Of course it is also possible to use mixtures of aliphatic amino alcohols or mixtures of alkanediols or mixtures of diaminoalkanes in the respective reactions. The resulting polyalkylenepolyamines can comprise alkylene units of different length. In this case at least one of the starting materials comprises an alkyl group or alkylene group having five or more carbon atoms.

Polyfunctional amino alcohols having more than one OH group or more than one primary or secondary amino group can also be reacted with one another. In this case, highly branched products are obtained. Examples of polyfunctional amino alcohols are diethanolamine, N-(2-aminoethyl)ethanolamine, diisopropanolamine, diisononanolamine, diisodecanolamine, diisoundecanolamine, diisododecanolamine, diisotridecanolamine. In this case at least one of the starting materials comprises an alkyl group or alkylene group having five or more carbon atoms.

Polyols or mixtures of diols and polyols can also be reacted with diamines. Polyamines or mixtures of diamines and polyamines can also be reacted with diols. Polyols or mixtures of diols and polyols can also be reacted with polyamines or mixtures of diamines and polyamines. It is also possible to react polyamine polyols or mixtures of polyamine polyols with diols, diamines or alcohol amines. In this case, highly branched products are obtained. Examples of polyols are glycerol, trimethylolpropane, sorbitol, triethanolamine, triisopropanolamine. Examples of polyamines are diethylenetriamine, tris(aminoethyl)amine, triazine, 3-(2-aminoethylamino)-propylamine, dipropylenetriamine, N,N"-bis(3-aminopropyl)ethylenediamine. In this case at least one of the starting materials comprises an alkyl group or alkylene group having five or more carbon atoms.

In one embodiment of the process of the invention, aliphatic polyalkylenepolyamines are reacted with aliphatic amino alcohols or with diamines or polyamines or with aliphatic diols or polyols to form lipophilic polyalkylenepolyamines.

Hydroxyl and amino groups in diols, polyols and diamines, polyamines are preferably used in molar ratios of from 20:1 to 1:20, particularly preferably in ratios of from 8:1 to 1:8, in particular from 3:1 to 1:3.

In one preferred embodiment of the process of the invention the heteroatoms N or O of one of the reactants—aliphatic amino alcohols, aliphatic diamines or polyamines or aliphatic diols or polyols—are located in alpha- and beta-position on the chain of C atoms. Alpha- and beta-position denotes the positions on two C atoms attached covalently to one another, with one of the C atoms being terminal.

In one preferred embodiment of the process of the invention the heteroatoms N or O of one of the reactants—aliphatic amino alcohols, aliphatic diamines or polyamines or aliphatic diols or polyols—are located in alpha- and omega-position on the chain of C atoms. Alpha- and omega-position denotes that the two heteroatoms are attached to terminal C atoms, which are located at opposite ends of the chain of the C atoms.

The catalyst generally comprises at least one element of the sub-groups of the Periodic Table of the Elements (transition metal).

The process according to the invention of alcohol amination can be carried out in the presence or absence of an additional solvent.

The alcohol amination according to the invention can be carried out in a multiphase, preferably one-phase or two-phase, liquid system at temperatures of generally 20 to 250° C. After the end of the reaction and optionally after the addition of a further solvent, there is a two-phase reaction system present. In this system, one phase, often the upper phase, comprises substantially the majority of the lipophilic polyalkylenepolyamines formed, and optionally an apolar solvent, and also apolar reactants still present. The second phase, often the lower phase, comprises substantially water and optionally a polar solvent and also, preferably, the homogeneously dissolved catalyst.

In one preferred embodiment of the process of the invention a polar solvent, as for example water, dimethylformamide, dimethyl sulfoxide, ionic liquids, methanol or ethanol, preferably water, is added to the reaction mixture after the reaction, more particularly after cooling to room temperature. The addition of the polar solvent generally supports the phase separation after the reaction.

As is known to the skilled person from his or her common general knowledge, a phase separation is never complete—in other words, small amounts, for example up to 5%, of the apolar compounds may also be in solution in the second phase, and small amounts, for example up to 5%, of the polar compounds may also be in solution in the first phase.

In one preferred embodiment of the invention, alkylenediamines having 2 or more carbon atoms (C atoms) in the linear or branched alkylene chain are reacted with alkanediols having five or more C atoms in the linear or branched alkylene chain, or alkylenediamines having five or more C atoms in the linear or branched alkylene chain are reacted with alkanediols having 2 or more C atoms in the linear or branched alkylene chain, in the presence of a catalyst (cf., by way of example, equation 1):

Equation 1

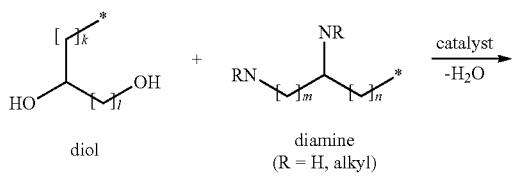

diol diamine
(R = H, alkyl)

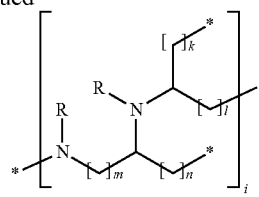

polyalkylenepolyamines

Preferred alkylenediamines are ethylenediamine, 1,3-propylenediamine, 1,2-propylenediamine, butylenediamine, for example 1,4-butylenediamine or 1,2-butylenediamine, diaminopentane, for example 1,5-diaminopentane or 1,2-diaminopentane, diaminohexane, for example 1,6-diaminohexane or 1,2-diaminohexane, diaminoheptane, for example 1,7-diaminoheptane or 1,2-diaminoheptane, diaminooctane, for example 1,8-diaminooctane or 1,2-diaminooctane, diaminononane, for example 1,9-diaminononane or 1,2-diaminononane, diaminodecane, for example 1,10-diaminodecane or 1,2-diaminodecane, diaminoundecane, for example 1,11-diaminoundecane or 1,2-diaminoundecane, diaminododecane, for example 1,12-diaminododecane or 1,2-diaminododecane, 3,3"-dimethyl-4,4"-diaminodicyclohexylmethane, 4,4"-diaminodicyclohexylmethane, isophoronediamine, 2,2-dimethylpropane-1,3-diamine, 4,7,10-trioxamidecane-1,13-diamine, 4,9-dioxadodecane-1,12-diamine, polyetheramines, piperazine, 3-(cyclohexylamino)propylamine, 3-(methylamino)propylamine, N,N-bis(3-aminopropyl)methylamine.

Particularly preferred are 1,9-nonanediol, 1,2-decanediol, 1,10-decanediol, 1,2-dodecanediol, 1,12-dodecanediol, ethanediol, 1,2-propanediol, 1,3-propanediol.

Preferred alkylenediamines are ethylenediamine, 1,3-propylenediamine, 1,2-propylenediamine, butylenediamine, for example 1,4-butylenediamine or 1,2-butylenediamine, diaminopentane, for example 1,5-diaminopentane or 1,2-diaminopentane, 1,5-diamino-2-methylpentane, diaminohexane, for example 1,6-diaminohexane or 1,2-diaminohexane, diaminoheptane, for example 1,7-diaminoheptane or 1,2-diaminoheptane, diaminooctane, for example 1,8-diaminooctane or 1,2-diaminooctane, diaminononane, for example 1,9-diaminononane or 1,2-diaminononane, diaminodecane, for example 1,10-diaminodecane or 1,2-diaminodecane, diaminoundecane, for example 1,11-diaminoundecane or 1,2-diaminoundecane, diaminododecane, for example 1,12-diaminododecane or 1,2-diaminododecane, 3,3"-dimethyl-4,4"-diaminodicyclohexylmethane, 4,4"-diaminodicyclohexylmethane, isophoronediamine, 2,2-dimethylpropane-1,3-diamine, 4,7,10-trioxamidecane-1,13-diamine, 4,9-dioxadodecane-1,12-diamine, polyetheramines, piperazine, 3-(cyclohexylamino)propylamine, 3-(methylamino)propylamine, N,N-bis(3-aminopropyl)methylamine.

Particularly preferred are ethylenediamine, 1,2-propylenediamine, 1,3-propylenediamine, 1,5-diamino-2-methylpentane, hexamethylenediamine, 1,9-diaminononane, 1,10-diaminodecane, 1,12-diaminododecane.

Particularly preferred is the reaction of either (i) ethylenediamine or (ii) 1,3-propylenediamine with either a) 1,2-decanediol or b) 1,2-dodecanediol or (iii) 1,2-propylenediamine with either a) 1,2-decanediol or b) 1,2-dodecanediol in the presence of a catalyst to give the polyalkanolpolyamine.

The number of repeating units i of the polyamine is generally between 3 and 50 000.

The polyalkanolamines thus obtained can carry both $NH_2$ and also OH groups as end groups at the chain ends.

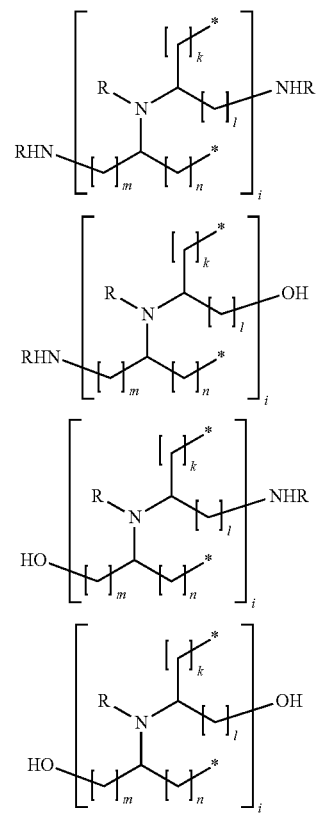

where preferably

R independently of one another, are identical or different and are H, $C_1$-$C_{50}$-alkyl, l, m independently of one another, are identical or different and are an integer from the range from 1 to 50, preferably from 1 to 30, particularly preferably from 1 to 20, n, k independently of one another, are identical or different and are an integer from the range from 0 to 50, preferably from 0 to 30, particularly preferably from 0 to 20, i is an integer from the range from 3 to 50 000.

The number-average molecular weight Mn of the polyalkanolamines obtained is generally from 200 to 2 000 000, preferably from 400 to 750 000 and particularly preferably from 400 to 100 000. The value of the polydispersity index (Mw/Mn) is generally in the range from 1.2 to 20, preferably from 1.5-7.5. The cationic charge density (at pH 4-5) is generally in the range from 0.1 to 22 mequ/g of dry substance, preferably in the range from 0.5 to 10 mequ/g, particularly preferably in the range from 0.5 to 5 mequ/g.

The lipophilic polyalkanolamines obtained according to the process according to the invention can be present either in linear form or in branched or multi-branched form, and also have ring-shaped structural units:

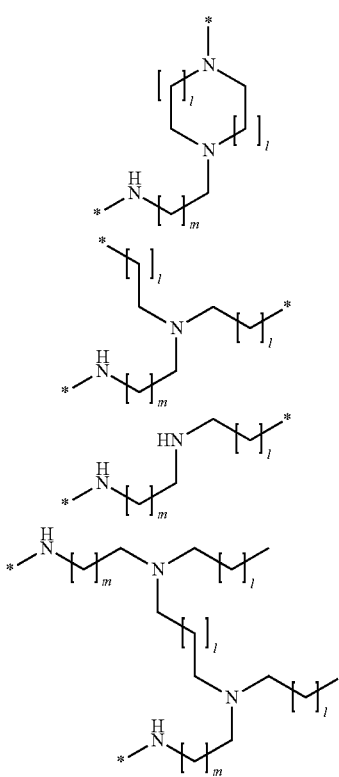

In this connection, the distribution of the structural units (linear, branched or cyclic) is random. The lipophilic polyalkanolamines thus obtained differ from the polyethyleneimines prepared from ethyleneimine in particular by virtue of the OH end groups present and also by virtue of the lipophilic alkylene groups or alkyl groups.

In another preferred embodiment of the invention a linear or branched amino alcohol having five or more C atoms is reacted in the presence of a catalyst:

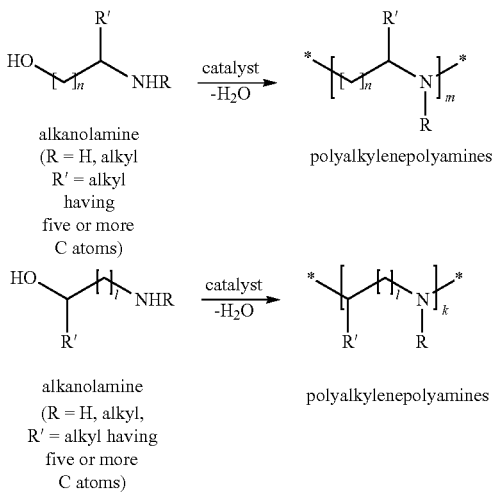

Examples are 2-aminohexan-1-ol, 5-amino-2,2-dimethylpentanol, 2-aminohexan-1-ol, 2-aminoheptan-1-ol, 2-aminooctan-1-ol, 2-aminononan-1-ol, 2-aminodecan-1-ol, 2-aminoundecan-1-ol, 2-aminodocedan-1-ol, 2-aminotridecan-1-ol, 2-aminoisohexan-1-ol, 2-aminoisoheptan-1-ol, 2-aminoisooctan-1-ol, 2-aminoisononan-1-ol, 2-aminoisodecan-1-ol, 2-aminoisoundecan-1-ol, 2-aminoisodocedan-1-ol, 2-aminoisotridecan-1-ol.

In another preferred embodiment of the invention a linear alpha, omega-amino alcohol having five or more C atoms in the alkylene chain is reacted in the presence of a catalyst.

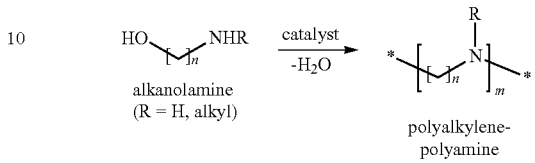

Examples are alkanolamines such as 6-aminohexan-1-ol, 7-aminoheptan-1-ol, 8-aminooctan-1-ol, 9-aminononan-1-ol, 10-aminodecan-1-ol, 11-aminoundecan-1-ol, 11-aminoundecan-1-ol, 12-aminododecan-1-ol, 13-aminotridecan-1-ol.

In another preferred embodiment of the invention, a linear alpha,beta-amino alcohol having five or more C atoms in the alkyl group is reacted in the presence of a catalyst.

Examples are alkanolamines such as 2-aminoheptan-1-ol, 2-aminooctan-1-ol, 2-aminononan-1-ol, 2-aminodecan-1-ol, 2-aminoundecan-1-ol, 2-aminoundecan-1-ol, 2-aminododecan-1-ol, 2-aminotridecan-1-ol.

The catalyst is preferably a transition metal complex catalyst which comprises one or more different metals of the sub-groups of the Periodic Table of the Elements, preferably at least one element from groups 8, 9 and 10 of the Periodic Table of the Elements, particularly preferably ruthenium or iridium. During the reaction the catalyst is present in homogeneous solution in the reaction medium.

The specified sub-group metals are preferably present in the form of complex compounds. Numerous different ligands are contemplated.

Suitable ligands present in the transition metal complex compounds are, for example, phosphines substituted with alkyl or aryl, polydentate phosphines substituted with alkyl or aryl which are bridged via arylene or alkylene groups, nitrogen-heterocyclic carbenes, cyclopentanedienyl and pentamethylcyclopentadienyl, aryl, olefin ligands, hydride, halide, carboxylate, alkoxylate, carbonyl, hydroxide, trialkylamine, dialkylamine, monoalkylamine, nitrogen aromatics such as pyridine or pyrrolidine and polydentate amines. The organometallic complex can comprise one or more different specified ligands.

Preferred ligands are (monodentate) phosphines or (polydentate) polyphosphines, for example diphosphines, with at least one unbranched or branched, acyclic or cyclic, aliphatic, aromatic or araliphatic radical having 1 to 20, preferably 1 to 12 carbon atoms. Examples of branched cycloaliphatic and araliphatic radicals are —CH$_2$—C$_6$H$_{11}$ and —CH$_2$—C$_6$H$_5$. Suitable radicals which may be mentioned by way of example are: methyl, ethyl, 1-propyl, 2-propyl, 1-butyl, 2-butyl, 1-(2-methyl)propyl, 2-(2-methyl)propyl, 1-pentyl, 1-hexyl, 1-heptyl, 1-octyl, 1-nonyl, 1-decyl, 1-undecyl, 1-dodecyl, cyclopentenyl, cyclohexyl, cycloheptyl and cyclooctyl, methylcyclopentyl, methylcyclohexyl, 1-(2-methyl)pentyl, 1-(2-ethyl)hexyl, 1-(2-propylheptyl), adamantyl and norbornyl, phenyl, tolyl and xylyl, and 1-phenylpyrrole, 1-(2-methoxyphenyl)pyrrole, 1-(2,4,6-trimethylphenyl)imidazole and 1-phenylindole. The phosphine group can comprise two or three of the specified unbranched or branched, acyclic or cyclic, aliphatic, aromatic or araliphatic radicals. These may be identical or different.

In the specified unbranched or branched, acyclic or cyclic, aliphatic, aromatic or araliphatic radicals, individual carbon atoms can also be substituted by further phosphine groups. Also comprised are thus polydentate, for example bi- or tridentate, phosphine ligands, the phosphine groups of which are bridged by alkylene or arylene groups. The phosphine groups are preferably bridged by 1,2-phenylene, methylene, 1,2-ethylene, 1,2-dimethyl-1,2-ethylene, 1,3-propylene, 1,4-butylene and 1,5-propylene bridges.

Particularly suitable monodentate phosphine ligands are triphenylphosphine, tritolylphosphine, tri-n-butylphosphine, tri-n-octylphosphine, trimethylphosphine and triethylphosphine, triphenylphosphane trisulfonate, triethanolphosphine, 1,3,5-triaza-7-phosphatricyclo-[3.3.1.13,7]decane, di(1-adamantyl)-n-butylphosphine, di(1-adamantyl)benzylphosphine, 2-(dicyclohexylphosphino)-1-phenyl-1H-pyrrole, 2-(dicyclohexylphosphino)-1-(2,4,6-trimethylphenyl)-1H-imidazole, 2-(dicyclohexylphosphino)-1-phenylindole, 2-(di-tert-butylphosphino)-1-phenylindole, 2-(dicyclohexylphosphino)-1-(2-methoxyphenyl)-1H-pyrrole, 2-(di-tert-butylphosphino)-1-(2-methoxyphenyl)-1H-pyrrole and 2-(di-tert-butylphosphino)-1-phenyl-1H-pyrrole. Very particular preference is given to tri-n-butylphosphine, tri-n-octylphosphine, triphenylphosphane trisulfonate, triethanolphosphine, 1,3,5-triaza-7-phosphatricyclo-[3.3.1.13,7]decane, di(1-adamantyl)-n-butylphosphine, di(1-adamantyl)benzylphosphine, 2-(dicyclohexylphosphino)-1-phenyl-1H-pyrrole, in particular if, as already described, a polar solvent is added after the reaction. Especially preferred in this case are those ligands which form water-soluble complexes with Ru.

Particularly suitable polydentate phosphine ligands are bis(diphenylphosphino)methane, 1,2-bis(diphenylphosphino)ethane, 1,2-dimethyl-1,2-bis(diphenylphosphino)ethane, 1,2-bis(dicyclohexylphosphino)ethane, 1,2-bis(diethylphosphino)ethane, 1,3-bis(diphenyl-phosphino)propane, 1,4-bis(diphenylphosphino)butane, 2,3-bis(diphenylphosphino)butane, 1,3-bis(diphenylphosphino)propane, 1,1,1-tris(diphenylphosphinomethyl)ethane, 1,1'-bis-(diphenylphosphanyl)ferrocene and 4,5-bis(diphenylphosphino)-9,9-dimethylxanthene.

Furthermore, mention may be made of nitrogen-heterocyclic carbenes as particularly suitable ligands. Preference is given to 1-butyl-3-methylimidazolin-2-ylidene, 1-ethyl-3-methylimidazolin-2-ylidene, 1-methylimidazolin-2-ylidene, 1,3-bis(2,4,6-trimethylphenyl)imidazolin-2-ylidene, 1-butyl-3-methylimidazolin-2-ylidene and dipropylimidazolin-2-ylidene, in particular if, as already described, a polar solvent is added after the reaction. Particular preference is given to 1-butyl-3-methylimidazolin-2-ylidene, 1-ethyl-3-methylimidazolin-2-ylidene, 1-methylimidazolin-2-ylidene. Especially preferred in this case are those ligands which form water-soluble complexes with Ru. Particularly suitable ligands which may be mentioned are also cyclopentadienyl and its derivatives mono- to pentasubstituted with alkyl, aryl and/or hydroxy, such as, for example, methylcyclopentadienyl, pentamethylcyclopentadienyl, tetraphenylhydroxycyclopentadienyl and pentaphenylcyclopentadienyl. Further particularly suitable ligands are indenyl and its substituted derivatives. Likewise particularly suitable ligands are hydroxide, chloride, hydride and carbonyl, especially if, as already described, a polar solvent is added after the reaction.

The transition metal complex catalyst can comprise two or more different ligands from all the ligands described above. Especially preferred in this case are those ligands or ligand combinations which form water-soluble complexes with Ru.

The homogeneous catalysts can be used either directly in their active form or else be produced starting from customary standard complexes such as, for example, [Ru(p-cymene)Cl$_2$]$_2$, [Ru(benzene)Cl$_2$]$_n$, [Ru(CO)$_2$Cl$_2$]$_n$, [Ru(CO)$_3$Cl$_2$]$_2$, [Ru(COD)(allyl)], [RuCl$_3$*H$_2$O], [Ru(acetylacetonate)$_3$], [Ru(DMSO)$_4$Cl$_2$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$], [Ru(cyclopentadienyl)(PPh$_3$)$_2$Cl], [Ru(cyclopentadienyl)(CO)$_2$Cl], [Ru(cyclopentadienyl)(CO)$_2$H], [Ru(cyclopentadienyl)(CO)$_2$]$_2$, [Ru(pentamethylcyclopentadienyl)(CO)$_2$Cl], [Ru(pentamethylcyclopentadienyl)(CO)$_2$H], [Ru(pentamethylcyclopentadienyl)(CO)$_2$]$_2$, [Ru(indenyl)(CO)$_2$Cl], [Ru(indenyl)(CO)$_2$H], [Ru(indenyl)(CO)$_2$]$_2$, ruthenocene, [Ru(binap)Cl$_2$], [Ru(bipyridine)$_2$Cl$_2$*2H$_2$O], [Ru(COD)Cl$_2$]$_2$, [Ru(pentamethylcyclopentadienyl)(COD)Cl], [Ru$_3$(CO)$_{12}$], [Ru(tetraphenylhydroxy-cyclopentadienyl)(CO)$_2$H], [Ru(PMe$_3$)$_4$(H)$_2$], [Ru(PEt$_3$)$_4$(H)$_2$], [Ru(PnPr$_3$)$_4$(H)$_2$], [Ru(PnBu$_3$)$_4$(H)$_2$], [Ru(PnOctyl$_3$)$_4$(H)$_2$], [IrCl$_3$*H$_2$O], KIrCl$_4$, K$_3$IrCl$_6$, [Ir(COD)Cl]$_2$, [Ir(cyclooctene)$_2$Cl]$_2$, [Ir(ethene)$_2$Cl]$_2$, [Ir(cyclopentadienyl)Cl$_2$]$_2$, [Ir(pentamethylcyclopentadienyl)Cl$_2$]$_2$, [Ir(cyclopenta-dienyl)(CO)$_2$], [Ir(pentamethylcyclopentadienyl)(CO)$_2$], [Ir(PPh$_3$)$_2$(CO)(H)], [Ir(PPh$_3$)$_2$(CO)(Cl)], [Ir(PPh$_3$)$_3$(Cl)] with the addition of the corresponding ligands, preferably the aforementioned mono- or polydentate phosphine ligands or the aforementioned nitrogen-heterocyclic carbenes, only under the reaction conditions.

The amount of the metal component in the catalyst, preferably ruthenium or iridium, is generally 0.1 to 5000 ppm by weight, in each case based on the total liquid reaction mixture.

The process according to the invention in step (a) can be carried out either in a solvent or without solvent. The process according to the invention can of course also be carried out in a solvent mixture.

If the process according to the invention is carried out in a solvent, then the amount of solvent is often selected such that the starting materials (i) and (ii) just dissolve in the solvent. In general, the weight ratio of the amount of solvent to the amount of starting materials (i) and (ii) is from 100:1 to 0.1:1, preferably from 10:1 to 0.1:1.

If the reaction is carried out without solvent, then after the reaction, in particular after the cooling to ambient temperature, and optionally after the addition of a solvent or solvent mixture, a nonpolar phase and a polar aqueous phase are present. After the reaction, the homogeneous catalyst is preferably present in dissolved form in the polar phase, whereas the product is present in the nonpolar phase. If the catalyst is in the polar phase, then it can be separated off from product by phase separation. If the catalyst is partially or completely present in the nonpolar phase, then it can remain in the product or can be depleted from this by an optionally multiple extraction with a suitable solvent. The extractant used is preferably a strongly polar solvent which, following concentration by evaporation, can, optionally together with the extracted catalyst, be used again for the reaction. Suitable extractants are e.g. water, methanol, ethanol, dimethyl sulfoxide, dimethylformamide, ionic liquids such as e.g. 1-ethyl-3-methylimidazolium hydrogensulfate or 1-butyl-3-methylimidazolium methanesulfonate. It is also possible to remove the catalyst using a suitable absorber material. Separation can also take place by adding water or an ionic liquid to the product phase if the reaction is carried out in a solvent which is immiscible with water and/or the ionic liquid. If, in this connection, the catalyst dissolves preferentially in water or the ionic liquid, it can be separated off with the solvent from the organic product phase and optionally be reused. This can be effected by choosing suitable ligands.

If the reaction is carried out in a solvent, then this may be miscible with the product and can be separated off after the reaction by distillation. Suitable solvents are e.g. toluene, benzene, xylene, alkanes, e.g. hexanes, heptanes or octanes, acyclic and cyclic ethers such as diethyl ether or tetrahydrofuran, and also alcohols having more than three carbon atoms, in which the OH group is bonded to a tertiary carbon atom, for example tert-amyl alcohol. Preference is given to benzene, toluene, xylenes, alkanes, acyclic and cyclic ethers or alcohols having more than three carbon atoms, in which the OH group is bonded to a tertiary carbon atom, particular preference being given to toluene and tert-amyl alcohol. During the distillation, it is also possible to separate off unreacted, in particular nonpolar, starting materials.

It is also possible to use solvents which have a miscibility gap with the product or the starting materials. As a result of suitable selection of the ligands, the catalyst dissolves preferentially in the polar phase. Suitable solvents in this case are e.g. water, sulfoxides such as dimethyl sulfoxide, formamides such as dimethylformamide, ionic liquids such as e.g. 1-ethyl-3-methylimidazolium hydrogensulfate and 1-butyl-3-methylimidazolium methanesulfonate, preferably water and ionic liquids.

The solvent can also be miscible under the reaction conditions with the starting materials and the product and a polar phase such as water or ionic liquid and only after cooling form a second liquid phase which comprises the product. The majority of the catalyst is dissolved in the polar phase. This phase can, moreover, also comprise a fraction of the starting materials. The catalyst can then be separated off together with the polar phase and be reused. The fraction of catalyst present in the product can then be separated off by extraction, suitable absorber materials such as, for example, polyacrylic acid and salts thereof, sulfonated polystyrenes and salts thereof, activated carbons, montmorillonites, bentonites and also zeolites, or else can be left in the product.

In the case of the variant of the two-phase reaction procedure, suitable nonpolar solvents are particularly toluene, benzene, xylenes, alkanes, such as hexanes, heptanes and octanes, in combination with polar or hydrophilic ligands on the transition metal catalyst such as nitrogen-heterocyclic carbenes, polar phosphanes or cationic or anionic ligands, as a result of which the transition metal catalyst accumulates in the polar phase. In this variant, in which the solvent forms a nonpolar phase with the product and the catalyst and also optionally unreacted starting materials, with the water of reaction and optionally a further solvent added after the reaction, forms a polar phase, the majority of the catalyst and optionally unreacted starting materials can be separated off from the product phase by simple phase separation and be reused.

If volatile by-products or unreacted starting materials or else the added solvent are undesired, these can be separated off from the product without problems by distillation.

In a further variant, the reaction is carried out in a polar solvent, in water or an ionic liquid. The product can be separated off by adding a nonpolar solvent which dissolves the product, but is immiscible with the solvent used for the reaction. Examples of the nonpolar solvent are toluene, benzene, alkanes, such as hexanes, heptanes or octanes, and acyclic or cyclic ethers, such as diethyl ether or tetrahydrofuran. If the catalyst dissolves preferentially in the polar phase, it can be separated off from the nonpolar product phase with the solvent and optionally be reused.

The reaction takes place in the liquid phase at a temperature of generally 20 to 250° C. Preferably, the temperature is at least 100° C. and preferably at most 200° C., in particular preferably the temperature is 130 to 180° C. The reaction can be carried out at a total pressure of from 0.1 to 25 MPa absolute, which may be either the intrinsic pressure of the solvent at the reaction temperature or else the pressure of a gas such as nitrogen, argon or hydrogen. The average reaction time is generally 15 minutes to 100 hours.

It may also be advantageous to remove the water formed during the reaction from the reaction mixture continuously. The water of reaction can be separated off directly by distillation from the reaction mixture or as an azeotrope with the addition of a suitable solvent (entrainer) and using a water separator, or be removed by adding water-withdrawing auxiliaries.

The addition of bases can have a positive effect on the product formation. Suitable bases which may be mentioned here are alkali metal hydroxides, alkaline earth metal hydroxides, alkali metal alcoholates, alkaline earth metal alcoholates, alkali metal carbonates and alkaline earth metal carbonates, of which 0.01 to 100 equivalents can be used based on the metal catalyst used.

A further subject of the invention are polyalkylenepolyamines which are prepared in accordance with the described embodiments of the process according to the invention.

In a preferred embodiment of the process according to the invention, the heteroatoms O or N of one of the starting materials (i) aliphatic amino alcohols, (ii) aliphatic diamines or polyamines or aliphatic diols or polyols are located in alpha and beta position on the chain of carbon atoms and thus on adjacent carbon atoms.

In a preferred embodiment of the process according to the invention, the heteroatoms O or N of one of the starting materials (i) aliphatic amino alcohols, (ii) aliphatic diamines or polyamines or aliphatic diols or polyols are located in alpha and omega position on the chain of carbon atoms and thus at opposite ends of the chain of carbon atoms.

A further subject of the invention are polyalkylenepolyamines which comprise hydroxyl groups, secondary amines or tertiary amines. The hydroxyl groups, secondary amines or tertiary amines are preferably located on a terminal carbon atom of an alkylene group and therefore constitute an end group. These polyalkylenepolyamines preferably comprise hydroxyl groups.

These polyalkylenepolyamines which comprise hydroxyl groups, secondary amines or tertiary amines are obtainable, for example, by means of the process according to the invention. More particularly these polyalkylenepolyamines are obtained in a process by the polymerization of monomers in one step.

Preferably the ratio of the number of hydroxyl end groups to amine end groups (primary, secondary, tertiary) is from 10:1 to 1:10, preferably from 5:1 to 1:5, more preferably from 2:1 to 1:2.

In a further preferred embodiment, those polyalkylenepolyamines which comprise hydroxyl groups, secondary amines or tertiary amines comprise only hydroxyl end groups or only amine end groups (primary, secondary, tertiary).

The invention also relates, furthermore, to the uses of these polyalkylenepolyamines a) as adhesion promoters for printing inks, b) as auxiliaries (adhesion) for the production of composite films, c) as cohesion promoters for adhesives, d) as crosslinkers/curing agents for resins, e) as primers in paints, f) as wet-adhesion promoters in emulsion paints, g) as complexing agents and flocculating agents, h) as penetration assistants in wood preservation, i) as corrosion inhibitors, j) as immobilizing agents for proteins and enzymes, k) as curing agents for epoxide resins.

The present invention provides processes for the preparation of lipophilic polyalkylenepolyamines in which no undesired co-products, for example ammonia, are formed.

The invention is illustrated in more detail by the examples without the examples limiting the subject matter of the invention.

EXAMPLES

The average molecular weight of the oligomers was determined by gel permeation chromatography in accordance with the method of size exclusion chromatography. The eluent used was hexafluoroisopropanol with 0.05% of potassium trifluoroacetate. The measurement was carried out at 40° C. with a flow rate of 1 ml/min on a styrene-divinylbenzene copolymer column (8 mm*30 cm) with an RI differential refractometer or UV photometer as detector. Calibration took place with narrow-range PMMA standards.

For the measurement of the Hazen color number (in accordance with APHA) the sample is diluted 1:2500 with a diluent which does not absorb in the range from 380 to 720 nm. The Hazen color number is then determined in a range from 380 to 720 nm in 10 nm steps.

Example 1

A 250 ml autoclave with paddle stirrer was charged under inert conditions, for the exclusion of oxygen, with 0.20 g (0.71 mmol) of [Ru(COD)Cl2], 0.50 g (2.9 mmol) of 1-butyl-3-methylimidazolium chloride, 12.1 g (0.06 mol) of 1,2-dodecanediol, 20.0 g (0.27 mol) of 1,3-propylenediamine, 0.50 g (4.46 mmol) of potassium tert-butoxide and 34 ml of toluene. The reaction mixture was stirred in the closed autoclave at 150° C. under the intrinsic pressure of the solvent for 20 hours. Following completed reaction and cooling, 5 ml of water were added to the reaction mixture, which was shaken, giving a solution (50.0 g) of the product in toluene and also an aqueous solution (12.66 g) of the catalyst. The phases were separated from one another and the catalyst phase was used again for Example 2. From the lipophilic product phase, the unreacted reactant and volatile constituents were removed on a rotary evaporator at 20 mbar and 120° C., giving 14.13 g of the pure product. The weight-average (RI) of the oligomer obtained was at 1470 g/mol, with a dispersity (Mw/Mn) of 3.9. This corresponds to an average chain length n for the oligomer $(CH_2CH(C_{10}H_{21}) NHCH_2CH_2NH)_n$ of 6. The color number was 74.

Example 2

A 250 ml autoclave with paddle stirrer was charged under inert conditions with the catalyst phase from Example 1 (12.66 g), 12.1 g (0.06 mol) of 1,2-dodecanediol, 20.0 g (0.27 mol) of 1,3-propylenediamine, and 34 ml of toluene. The reaction mixture was stirred in the closed autoclave at 150° C. under the intrinsic pressure of the solvent for 20 hours. Following completed reaction and cooling, 5 ml of water were added to the reaction mixture, which was shaken, giving a solution (49.67 g) of the product in toluene and also an aqueous solution (27.38 g) of the catalyst. The phases were separated. From the product phase, the unreacted reactant and volatile constituents were removed on a rotary evaporator at 20 mbar and 120° C., giving 11.53 g of the pure product. The weight-average (RI) of the oligomer obtained was at 1020 g/mol, with a dispersity (Mw/Mn) of 3.6. This corresponds to an average chain length n for the oligomer $(CH_2CH(C_{10}H_{21}) NHCH_2CH_2NH)_n$ of 4.2. The color number was 1.

Example 3

A 250 ml autoclave with paddle stirrer was charged under inert conditions with 0.20 g (0.71 mmol) of [Ru(COD)Cl2], 0.50 g (2.9 mmol) of 1-butyl-3-methylimidazolium chloride, 12.1 g (0.06 mol) of 1,2-dodecanediol, 20.0 g (0.27 mol) of 1,3-propylenediamine, 0.50 g (4.46 mmol) of potassium tert-butoxide and 34 ml of toluene. In the closed autoclave, hydrogen was injected to 40 bar. Then the reaction mixture was heated at 150° C. and stirred for 20 hours. Following completed reaction and cooling, 20 ml of water were added to the reaction mixture, which was shaken, giving a solution of the product in toluene and also an aqueous solution of the catalyst. The phases were separated. From the product phase, the unreacted reactant and volatile constituents were removed on a rotary evaporator at 20 mbar and 120° C., giving 11.97 g of the pure product. The weight-average (RI) of the oligomer obtained was at 1470 g/mol, with a dispersity (Mw/Mn) of 3.9. This corresponds to an average chain length n for the oligomer $(CH_2CH(C_{10}H_{21}) NHCH_2CH_2NH)_n$ of 6. For the measurement of the color number, the product was diluted 2500-fold in toluene. The color number was 21.

Example 4

A 250 ml autoclave with paddle stirrer was charged under inert conditions with 0.20 g (0.71 mmol) of [Ru(COD)Cl2], 0.50 g (2.9 mmol) of 1-butyl-3-methylimidazolium chloride, 0.50 g (4.46 mmol) of potassium tert-butoxide, 9.71 g of the discharge from Example 1 and 34 ml of toluene. The reaction mixture was stirred in the closed autoclave at 140° C. under the intrinsic pressure of the solvent for 20 hours. Following completed reaction and cooling, 20 ml of water were added to the reaction mixture, which was shaken, giving a solution of the product in toluene and also an aqueous solution of the catalyst. The phases were separated. From the product phase, the unreacted reactant and volatile constituents were removed on a rotary evaporator at 20 mbar and 120° C., giving 8.82 g of the pure product. The weight-average (RI) of the oligomer obtained was at 1740 g/mol, with a dispersity (Mw/Mn) of 3.7. This corresponds to an average chain length n for the oligomer $(CH_2CH(C_{10}H_{21}) NHCH_2CH_2NH)_n$ of 7.3. For the measurement of the color number, the product was diluted 2500-fold in toluene. The color number was 200.

Example 5

A 250 ml autoclave with paddle stirrer was charged under inert conditions with 0.20 g (0.71 mmol) of [Ru(COD)Cl2], 0.50 g (2.9 mmol) of 1-butyl-3-methylimidazolium chloride, 12.1 g (0.06 mol) of 1,2-dodecanediol, 20.0 g (0.27 mol) of 1,3-propylenediamine, 0.50 g (4.46 mmol) of potassium tert-butoxide and 34 ml of toluene. The reaction mixture was stirred in the closed autoclave at 130° C. under the intrinsic pressure of the solvent for 30 hours. Following completed reaction and cooling, 20 ml of water were added to the reaction mixture, which was shaken, giving a solution of the product in toluene and also an aqueous solution of the catalyst. The phases were separated. From the product phase, the unreacted reactant and volatile constituents were removed on a rotary evaporator at 20 mbar and 120° C., giving 14.06 g of the pure product. The weight-average (RI) of the oligomer obtained was at 1110 g/mol, with a dispersity (Mw/Mn) of 4.3. This corresponds to an average chain length n for the oligomer $(CH_2CH(C_{10}H_{21})NHCH_2CH_2NH)_n$ of 4.6. The color number was 56.

Example 6

A 250 ml autoclave with paddle stirrer was charged under inert conditions with 0.20 g (0.71 mmol) of [Ru(COD)Cl2], 0.50 g (2.9 mmol) of 1-butyl-3-methylimidazolium chloride, 12.1 g (0.06 mol) of 1,2-dodecanediol, 20.0 g (0.27 mol) of 1,3-propylenediamine, 0.50 g (4.46 mmol) of potassium tert-butoxide and 34 ml of toluene. The reaction mixture was stirred in the closed autoclave at 170° C. under the intrinsic pressure of the solvent for 10 hours. Following completed reaction and cooling, 20 ml of water were added to the reaction mixture, which was shaken, giving a solution of the product in toluene and also an aqueous solution of the catalyst. The phases were separated. From the product phase, the unreacted reactant and volatile constituents were removed on a rotary evaporator at 20 mbar and 120° C., giving 14.18 g of the pure product. The weight-average (RI) of the oligomer obtained was at 1220 g/mol, with a dispersity (Mw/Mn) of 37. This corresponds to an average chain length n for the oligomer $(CH_2CH(C_{10}H_{21})NHCH_2CH_2NH)$, of 5.1. The color number was 73.

Example 7

A 250 ml autoclave with paddle stirrer was charged under inert conditions with 0.20 g (0.71 mmol) of [Ru(COD)Cl2], 0.50 g (2.9 mmol) of 1-butyl-3-methylimidazolium chloride, 12.1 g (0.06 mol) of 1,2-dodecanediol, 20.0 g (0.27 mol) of 1,3-propylenediamine, 0.50 g (4.46 mmol) of potassium tert-butoxide and 17 ml of toluene. The reaction mixture was stirred in the closed autoclave at 150° C. under the intrinsic pressure of the solvent for 20 hours. Following completed reaction and cooling, 20 ml of water were added to the reaction mixture, which was shaken, giving a solution of the product in toluene and also an aqueous solution of the catalyst. The phases were separated. From the product phase, the unreacted reactant and volatile constituents were removed on a rotary evaporator at 20 mbar and 120° C., giving 13.72 g of the pure product. The weight-average (RI) of the oligomer obtained was at 1280 g/mol, with a dispersity (Mw/Mn) of 3.8. This corresponds to an average chain length n for the oligomer $(CH_2CH(C_{10}H_{21})NHCH_2CH_2NH)_n$ of 5.3. The color number was 69.

Example 8

A 250 ml autoclave with paddle stirrer was charged under inert conditions with 0.25 g (0.89 mmol) of [Ru(COD)Cl2], 0.30 g (1.48 mmol) of tri-n-butylphosphine, 12.1 g (0.069 mol) of 1,2-decanediol, 25.0 g (0.42 mol) of 1,2-ethylenediamine, 0.10 g (0.89 mmol) of potassium tert-butoxide and 30 ml of toluene. The reaction mixture was stirred in the closed autoclave at 150° C. under the intrinsic pressure of the solvent for 30 hours. Following completed reaction and cooling, a brown discharge (64.3 g) was obtained, from which the unreacted reactant and volatile constituents were removed on a rotary evaporator at 12 mbar and 110° C. This gave 14.6 g of the product. The weight-average (RI) of the oligomer obtained was at 1380 g/mol, with a dispersity (Mw/Mn) of 2.4. This corresponds to an average chain length n for the oligomer $(CH_2CH(C_{10}H_{21})NHCH_2CH_2NH)_n$ of 7.

The invention claimed is:

1. A process for preparing a lipophilic polyalkylenepolyamine, by homogeneously catalyzed alcohol amination, the process comprising:
   (i) reacting aliphatic amino alcohols with one another, or
   (ii) reacting an aliphatic diamine or polyamine with an aliphatic diol or polyol, to obtain a reaction mixture, with elimination of water, in the presence of a homogeneous transition metal complex catalyst,
   wherein:
   at least one starting material of the aliphatic amino alcohols, aliphatic diamine, polyamine, aliphatic diol or polyol comprises an alkyl or alkylene group having five or more carbon atoms; and
   the process further comprises, after the reacting, performing a phase separation into a nonpolar phase and a polar phase, such that the lipophilic polyalkylenepolyamine is present in enriched form in the nonpolar phase.

2. The process according to claim 1, wherein at least one of the starting materials comprises an alkyl or alkylene group having from 5 to 50 carbon atoms.

3. The process according to claim 1, wherein the catalyst is present in enriched form in the polar phase.

4. The process according to claim 1, further comprising, after the reacting, adding a polar solvent to the reaction mixture.

5. The process according to claim 1, wherein the catalyst comprises a nitrogen-heterocyclic carbene ligand.

6. The process according to claim 1, wherein the catalyst comprises a monodentate or polydentate phosphine ligand.

7. The process according to claim 1, wherein the catalyst comprises at least one ligand selected from the group consisting of cyclopentadienyl, a substituted cyclopentadienyl, indenyl and a substituted indenyl.

8. The process according to claim 1, wherein the catalyst comprises at least one ligand selected from the group consisting of hydroxide, hydride, carbonyl and chloride.

9. The process according to claim 1, wherein the reaction is carried out in the presence of a solvent or solvent mixture.

10. The process according to claim 1, wherein heteroatoms O or N of one of the starting materials are located in alpha and beta position on a chain of carbon atoms and thus on adjacent carbon atoms.

11. The process according to claim 1, wherein heteroatoms O or N of one of the starting materials are located in alpha and omega position on a chain of carbon atoms and thus at opposite ends of the chain of carbon atoms.

12. A polyalkylenepolyamine obtained by the process according to claim 1, wherein a polydispersity of the polyalkylenepolyamine ranges from 2.4 to 37.

13. The polyalkylenepolyamine of claim 12, comprising a hydroxyl group, secondary amine or tertiary amine.

14. A process for promoting adhesion, the process comprising adding the polyalkylenepolyamine according to claim 12 to an adhesive, wherein the polyalkylenepolyamine is an adhesion promoter for at least one selected from the group consisting of
   printing inks,
   composite films, and
   emulsion paints.

15. The process according to claim 1, comprising
(i) reacting the aliphatic amino alcohols with one another.

16. The process according to claim 1, comprising
(ii) reacting the aliphatic diamine or polyamine with the aliphatic diol or polyol.

17. The process according to claim 4, wherein the catalyst comprises at least one ligand selected from the group consisting of hydroxide, hydride, carbonyl and chloride.

* * * * *